United States Patent [19]

Mattison et al.

[11] Patent Number: 4,599,457
[45] Date of Patent: Jul. 8, 1986

[54] PROCESS OF PREPARING HYDROXYARYLALDEHYDES

[75] Inventors: Phillip L. Mattison, New Brighton; LeRoy Krbechek, Golden Valley, both of Minn.

[73] Assignee: Henkel Corporation, Minneapolis, Minn.

[21] Appl. No.: 714,149

[22] Filed: Mar. 20, 1985

[51] Int. Cl.⁴ .............................................. C07C 45/45
[52] U.S. Cl. .................................... 568/433; 568/313
[58] Field of Search ................................ 568/433, 313

[56] References Cited

FOREIGN PATENT DOCUMENTS 0106653  4/1984  European Pat. Off. ............ 568/433

*Primary Examiner*—Bernard Helfin
*Attorney, Agent, or Firm*—Ernest G. Szoke; Patrick J. Span; Robin M. Davis

[57] ABSTRACT

An improvement in the process for preparing hydroxyarylaldehydes is disclosed where a phenolic compound is reacted with formaldehyde, in the presence of a catalyst such as a titanium or zirconium containing catalyst, optionally in the presence of a catalyst promoter, wherein the improvement is the addition of a yield effective amount of a modifier having the formula:

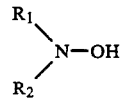

where $R_1$ is selected from the group consisting of: an alkyl group having from 1 to 12 carbon atoms, a cycloalkyl group that can have 5 and 6 carbon atoms, and an H, and where $R_2$ is selected from the group consisting of: an alkyl group having from 1 to 12 carbon atoms, and a cyclo alkyl group that can have 5 to 6 carbon atoms; and where $R_1$ and $R_2$ can together form a cyclic group that can have 5 and 6 carbon atoms.

14 Claims, No Drawings

PROCESS OF PREPARING HYDROXYARYLALDEHYDES

BACKGROUND OF THE INVENTION

This invention relates to the preparation of hydroxyarylaldehyes wherein a corresponding phenolic compound is reacted with formaldehyde, or a formaldehyde liberating compound in the presence of a catalyst such as a titanium or zirconium containing catalyst. Among other uses known to the art, the aldehydes are particularly useful as intermediates in the preparation of the corresponding oximes, which find utility as metal extractants.

The hydroxyarylaldehydes may be prepared by a number of routes. A summary and review of the synthesis of aromatic hydroxyaldehydes may be found in H. Fiege, K. Wedemehyer, K. A. Bauer, A. Krempel and R.G. Molleken, Frangrance Flavor Subst. Proc. Int. Haarmann Reimer Symp. 2nd, 1979 (Publ. 1980), pp. 63–73, which discusses in particular three processes of preparation.

One of these processes is the Reimer-Tiemann reaction which involves the reaction of a phenol with chloroform under very basis conditions to give the salicylaldehyde. Yields tend to be low and recovery of the product difficult. A recent patent, U.S. Pat. No. 4,324,922, relates to improvements in the process citing as further background Hans Wynberg, "Chemical Reviews", Vol. 60, 169 (1960) and Ferguson, "Chemical Reviews", Vol. 38, 229 (1946. Other U.S. Pat. Nos. 3,206,513 and 3,972,945 provide further background in relation thereto.

A second industrially useful approach involves condensation of the phenol with formaldehyde followed by oxidation with oxygen and a catalyst. While reasonable yields of salicylaldehyde are obtained, the process consists of two steps and involves the use of expensive catalysts. Illustrative of some of the patents relating to this process are U.S. Pat. Nos. 3,173,956, 3,321,526, 3,673,257, 3,780,110, 4,026,950 and 4,190,605.

Two other recent variations have been introduced. The first, which can be seen in U.S. Pat. No. 4,151,201, involves heating paraformaldehyde with phenol in the presence of anhydrous stannous chloride and pyridine. The second, which can be seen in U.S. Pat. No. 4,231,967, involves replacing the stannous chloride with an iron or chromium compound, preferably chromium acetylacetonate. Good yields are obtained via both processes. Both processes require relatively high levels of the catalyst promoter, pyridine, which must be recycled and requires special handling on an industrial scale. The presence of the heavy metals also presents problems in waste disposal. Further iron and chromium compounds tend to promote adverse side reactions.

Another process, which can be seen in U.S. Pat. No. 4,085,146 directed specifically towards production of alkylsalicylaldehydes, involves formation of a Mannich base, followed by oxidation and hydrolysis to the alkylsalicylaldehyde. While good yields are obtained, the process is economically burdensome due to the number of steps involved.

The invention herein finds particular utility in the process of preparing aldehydes using titanium or zirconium catalysts such as described in currently assigned, co-pending application U.S. Ser. No. 433,745 filed Oct. 12, 1982. Another similar process employing titanium catalysts in the preparation of alkylsalicylaldehyde in which the alkyl group contains from 1–10 carbon atoms is found in European Patent Publication 0077279 published Apr. 20, 1983.

It is an object of the instant invention to provide a method for improving the yield in the production of hydroxyarylaldehydes. Other objects will become apparent as this description proceeds.

SUMMARY OF THE INVENTION

The present invention provides an improvement in the production of hydroxyarylaldehydes, in which a phenolic compound (such as alkylphenol) is reacted with formaldehyde, or a formaldehyde liberating compound (such as paraformaldehyde) in the presence of a catalyst.

The invention is particularly useful with catalysts such as titanium or zirconium catalysts.

The improvement comprises conducting the reaction in the presence of a modifier in a sufficient amount to increase the yield of aldehydes (yield effective amount). The modifiers are certain hydroxylamines as defined further hereinbelow. Excellent yields are obtained in one step and when catalyst promoters, such as pyridine, are employed, less modifier is needed.

DETAILED DESCRIPTION OF THE INVENTION

As noted earlier, this invention is an improvement in production of hydroxyarylaldehydes in which a phenolic compound is reacted with formaldehyde in the presence of a catalyst, the improvement comprising the use of certain hydroxylamine modifiers in a yield effective amount.

The hydroxylamine modifiers of this invention may be defined by the formula

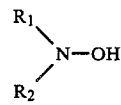

where $R_1$ is an alkyl group having 1–12 carbon atoms, or a cycloalkyl group having 5 or 6 carbon atoms and $R_2$ is H, an alkyl group having 1–12 carbon atoms or a cycloalkyl group having 5 or 6 carbon atoms provided that when $R_1$ and $R_2$ are both alkyl, both groups may together form a cyclic group.

Each alkyl group of the dialkylhydroxyl amine can suitably have from one up to twelve carbon atoms. Preferably the alkyl groups of the dialkylhydroxylamine has from about one to about 6 carbon atoms.

A more preferred range for the number of carbon atoms per group of the dialkylhydroxyl amine is from about 1 to about 3 carbon atoms. Most preferably each alkyl group of the dialkylhydroxylamine contains the same number of carbon atoms. The most preferred dialkylhydroxylamine modifier can therefore be selected from the group consisting of:
dimethylhydroxylamine,
diethylhydroxylamine, and
dipropylhydroxylamine.

When $R_1$ and $R_2$ form a cyclic group it is preferred that the cyclic structure or group contains 4 or 5 carbon atoms. When such cyclic group contains 4 carbon atoms the modifier is accordingly N-hydroxy pyrrolidine, and when the cyclic group contains 5 carbon atoms the modifier is accordingly N-hydroxy piperidine.

Modifiers called for by the instant invention are commercially available, or can be prepared by reacting hydroxylamine with the appropriate alkyl halide, and/or cycloalkyl halide. Suitably these reactions can be conducted at temperatures from about room temperature to about 70° C.

The improvement comprises conducting the reaction in the presence of a sufficient amount of a modifier to increase the yield of aldehyde (yield effective amount). The modifier is selected from the group consisting of: dialkylhydroxylamine; cycloalkylhydroxylamine; and dicycloalkylhydrosylamine. Excellent yields are obtained in one process step. When catalyst promoters such as pyridine are additionally used, less modifier is used.

In the present invention, the reaction temperature is desirably on the order of about 150°–250° C. Temperatures below 150° C. may be employed but this is undesirable as a long period of time would be required to complete the reaction. Moreover, side reactions can occur both at temperatures below 150° C. and above 250° C. giving results poor either in yields or quality. In any event, a temperature sufficiently high for the reaction of the phenolic compound and the formaldehyde within a practical time period is desired, while avoiding decomposition or adverse side reaction. The most desirable and preferred temperature range is generally found in the range of about 180°–220° C.

The process is generally carried out at greater than atmospheric pressure. About 2 hours are required for complete reaction at 180° C. with longer periods at the lower temperatures and shorter periods at higher temperatures. In general from about 0.5–8 hours is a practical time in which to carry out the reaction.

The reaction is generally conducted in a solvent system, utilizing conventional solvents for such reaction. The preferred solvent systems are the aromatic hydrocarbons such as toluene, benzene, xylene, chlorobenzene and isopropyl benzene; however, the aliphatic hydrocarbons and ethers, among those disclosed in U.S. Pat. No. 4,231,967, are also desirable solvents. As a practical matter, any solvent system for the reactants which does not strongly coordinate with the catalyst or otherwise substantially interfere with reaction is suitable.

Under the reaction conditions of this process, the preferred formaldehyde compounds to be used are formaldehyde and paraformaldehyde. The molar ratio of formaldehyde to phenolic compound is generally in the range of about 2–6:1 and preferably 3–5:1.

Preferably, the modifiers of the instant invention are added to the reaction mixture in concentrations relative to the phenolic compound used in the reaction. When no catalyst promoters are used, a modifier of the instant invention can acceptably be used in an amount up to about 25,000 parts per million (ppm) parts of the phenolic compound. Generally speaking, an acceptable minimum amount of modifier is about 5 ppm of the phenolic compound, with or without the addition of a catalyst promoter. A preferred concentration for the modifiers of the instant invention when no catalyst promoter is used, is from about 5 to about 2,500 ppm of the phenolic compound; and most preferably, the modifiers are added in an amount of from about 5 to about 500 ppm of the phenolic compound. When catalyst promoters such as pyridine are used, however, the hydroxyalkylamine modifiers of the instant invention can acceptably be used in an amount less than 100 ppm of the phenolic compound used; generally the acceptable minimum concentration is about 5 ppm of the phenolic compound used. A preferred concentration for these modifiers when a catalyst promoter is used is from about 5 to about 95 ppm of the phenolic compound; and the most preferred concentration is from about 5 to about 50 ppm of the phenolic compound.

The phenolic compounds useful in the present process are those having an available activated or unsubstituted position adjacent the phenolic, hydroxyl group, such as the ortho position of phenol. The present process appears selective for the ortho-position with no reaction at the paraposition. Thus the preferred compounds are those phenols having at least one unsubstituted ortho position available for reaction. Exemplary classes of phenolic compounds which are suitable for this invention are alkyl and aryl (including alkaryl and aralkyl) phenols, cycloalkyl phenols, alkoxy and aryloxy, acyl phenols and halophenols, as well as phenol itself. Thus, many of the phenolic compounds may be such as are found in U.S. Pat. Nos. 4,324,922, 4,231,967 and 4,151,201, and for the purpose of this invention may be defined by the following structural formula:

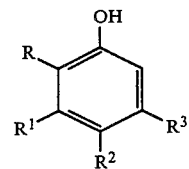

where R, $R^1$, $R^2$ and $R^3$, which can be the same or different, represent hydrogen atoms, alkyl, aryl, alkaryl, aralkyl, cycloalkyl, alkoxy, aryloxy, acyl groups or halogen. In these compounds the desirable alkyl groups generally contain from about 1–22 carbon atoms and the aryl group is phenyl. For those phenolic compounds which are to be converted to the corresponding oximes for use as metal extractants, the alkyl substituted compounds in which the alkyl groups contain from 8–22 carbon atoms, and preferably the 9 and 12 carbon atom groups, are the most desirable. Other desirable substituted phenols include cresol, tert-butylphenol (ortho and para), p-cumylphenol, cyclohexylphenol, 4-methoxyphenol, and o- or p-chlorophenol.

The preferred catalysts useful in the present invention are titanium or zirconium containing compounds and particularly titanium or zirconium (IV) compounds, or compounds in which the titanium or zirconium becomes oxidized to the (IV) state in the course of the reaction. Metallic titanium or zirconium itself is not suitable for use alone in the process. The particular catalyst employed is somewhat dependent upon the particular solvent and phenolic compound system employed in that the catalyst must be soluble in the system used to provide desirable results in yields and quality. Accordingly for the purpose of this invention, the catalyst contains an organic moiety to provide solubility in the system. The organic moiety may be introduced by preforming the catalyst to contain such moiety or by formation in situ in the course of the reaction.

Chelated titanium ester is a preferred catalyst for the instant invention. The chelated or complex compositions found most preferred in the present invention are the complexes of 2,4-pentanedionates, an 8-hydroxyquinoline complex and a salicylaldehyde (including the aldehydes formed by this invention) complex of the titanate esters. Particularly desirable are the reaction products of 8-hydroxyquinoline with titanium (IV) cresylate and/or titanium (IV) butoxide; the reaction products of salicylaldehyde with titanium cresylate; and titanium (IV) diisopropoxide bis (2,4-pentanedionate) and titanium (IV) oxide bis(2,4-pentanedionate). These complexes are generally preformed prior to reaction by mixing the desired titanate compound with the complexing compound for about 30 minutes. The molar ratio of catalyst to phenol is generally on the order of about 0.005 to 0.0005 and preferably in the range of 0.017 to 0.0005.

The preferred catalysts may also be represented by the formula:

(M) W,X,Y,Z where M represents titanium or zirconium, any one of W,X,Y and Z may be halide (preferably Cl, I or Br), alkoxy, aralkoxy, aryloxy, alkaryloxy, or acyloxy, cyclopentadienyl, or residues of a beta-diketone, 8-hydroxyquinoline or a salicylaldehyde, and when any two of W,X,Y,Z together are oxide, the other two are selected from the group of halogen, alkoxy, aralkoxy, aryloxy, alkaryloxy, acyloxy, a beta-diketon residue, (such as acetylacetone), an 8-hydroxyquinoline residue or a salicylaldehyde residue such as salicylaldehyde itself or substituted salicylaldehydes such as prepared by this invention, i.e. nonylsalicylaldehyde. Generally the alkyl portion of the alkoxy group will contain from 1 to 22 carbon atoms and the aryl portion is phenyl such as phenoxy.

Titanate polymers may also be employed as catalysts such as may be represented by the formula

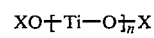

where n is an integer representing the number of repeating units and where X, which may be the same or different, is alkyl, aryl, alkaryl, or aralkyl, or a residue of a betadiketone such as acetyl acetone, or an 8-hydroxyquinoline, or a salicylaldehyde.

In order to further promote the reaction, a catalyst promoter may be added to the reaction system. These generally are unhindered aromatic amines, such as pyridine or quinoline such as 8-hydroxyquinoline, or phosphine oxides or phosphates, such as trioctylphosphine oxide and tributylphosphate.

This invention is further illustrated, but not limited, by the following examples in which all parts and percentages are by weight unless otherwise stated.

EXAMPLE 1

Four preparations of dodecylsalidylaldehyde (DSA) were made from a commercially available dodecylphenol. In three of the four preparations, diethylhydroxylamine (DHA) was added in an amount of 10 parts per million parts of the dodecylphenol.

The procedure employed was as follows: 800 ml of toluene was charged into a two liter, Parr stirred autoclave, model 4500, and heated to 220° C. A slurry containing:

63.0 g (2.0 moles at 95%) of paraformaldehyde,
2.1 g (0.02 moles) of pyridine,
50 ml of toluene,
1.81 g of cresyltitanate
for preparations a and b, no modifier; and
for preparation c, d and e, 10 parts of diethylhydroxylamine per million parts of dodecylphenol was pumped into the reactor. An additional 100 ml of toluene was then pumped into the reactor to insure the transfer of all the reactants. After 1½ hours at 210° C., the resulting product material was removed. The solvent was removed from this product under reduced pressure, and the resulting product was analyzed for the DSA by high pressure liquid chromatography (HPLC). The following indicates the percent of the theoretical yield of the product which was obtained:

| Percent of the Theoretical Yield of DSA | Parts Diethylhydroxylamine Per Million Parts Of Dodecylphenol |
|---|---|
| (a) 68% | 0 |
| (b) 68% | 0 |
| (c) 73% | 10 |
| (d) 72% | 10 |
| (e) 70% | 10 |

EXAMPLE 2

Two more preparations of the DSA were made using the same procedure as is described in Example I. Preparation (a) had 100 parts of diethylhydroxylamine modifier, and preparation (b) had 1000 parts of this modifier per million parts of the dodecylphenol.

The following indicates the percent of the theoretical yield of the product which was obtained:

| Percent of Theoretical Yield of DSA | Parts Diethylhydroxylamine Per Million Parts Of Dodecylphenol |
|---|---|
| (a) 66% | 100 |
| (b) 68% | 1000 |

What is claimed is:

1. In a process of preparing a hydroxyarylaldehyde wherein a phenolic compound is reacted with formaldehyde in the presence of a catalyst, the improvement wherein the reaction is conducted in the presence of a yield effective amount of a hydroxylamine modifier having the formula:

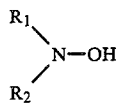

where $R_1$ is selected from the group consisting of: an alkyl group having from 1 to 12 carbon atoms, a cycloalkyl group that can have 5 and 6 carbon atoms, and an H, and where $R_2$ is selected from the group consisting of: an alkyl group having from 1 to 12 carbon atoms, and a cyclo alkyl group that can have 5 and 6 carbon atoms; and where $R_1$ and $R_2$ can together form a cyclic group that can have 5 and 6 carbon atoms 2. A process as defined in claim 1 wherein said catalyst is a titanium or zirconium catalyst.

3. A process as described in claim 2 wherein the modifier is added in an amount of up to 25,000 parts per million parts of the phenolic compound.

4. A process as described in claim 2 wherein pyridine is added as a catalyst promoter.

5. A process as described in claim 3 wherein less than 100 but greater than about 5 parts of the modifier is added per million parts of the phenolic compound.

6. A process as described in claim 2 wherein the modifier is added in an amount of from about 5 to about 2,500 parts per million parts of the phenolic compound.

7. A process as described in claim 6 wherein the modifier is a dialkylhydroxylamine having from about 1 to about 3 carbon atoms in each alkyl group.

8. A process as described in claim 2 wherein the modifier is added in an amount of from about 5 to about 500 parts per million parts of the phenolic compound.

9. A process as described in claim 2 wherein the modifier is a dialkylhydroxylamine selected from the group consisting of:
dimethylhydroxylamine,
diethylhydroxylamine, and
dipropylhydroxylamine.

10. A process as described in claim 9 wherein pyridine is present as a catalyst promoter.

11. A process as described in claim 10 wherein the modifier is present in an amount of less than 100 but greater than about 5 parts per million parts of the phenolic compound.

12. A process as described in claim 2 wherein the modifier is diethylhydroxylamine and is present in an amount of about 10 parts per million parts of the phenolic compound.

13. A process as described in claim 12 in which said phenolic compound is an alkylphenol in which said alkyl group contains from 1-22 carbon atoms.

14. A process as defined in claim 13 wherein said alkylphenol is dodecylphenol.

* * * * *